US006197089B1

(12) United States Patent
Frommeyer et al.

(10) Patent No.: US 6,197,089 B1
(45) Date of Patent: Mar. 6, 2001

(54) ACTIVATED MAGNESIUM METAL

(75) Inventors: Georg Frommeyer, Erkrath; Wilfried Knott; Andreas Weier, both of Essen, all of (DE)

(73) Assignee: Goldschmidt, A.G, Essen (DE)

(*) Notice: Subject to any disclaimer, the term of this patent is extended or adjusted under 35 U.S.C. 154(b) by 0 days.

(21) Appl. No.: 09/511,217

(22) Filed: Feb. 23, 2000

(30) Foreign Application Priority Data

Feb. 24, 1999 (DE) .............................. 199 07 856

(51) Int. Cl.[7] .......................... C22B 26/22; C22C 23/00; C07F 3/02
(52) U.S. Cl. ........................ 75/604; 420/590; 260/665 G
(58) Field of Search .............................. 75/604; 420/590; 260/665 G

(56) References Cited

U.S. PATENT DOCUMENTS 4,537,761 * 8/1985 Reed et al. ............................ 423/644
5,069,894 * 12/1991 Bogdanovic ......................... 423/647

OTHER PUBLICATIONS

Baker, K., et al., "Mechanical Activation of Magnesium Turnings for the Preparation of Reactive Grignard Reagents", *J. Org. Chem.* 56, pp. 698–703, (1991). No month.

Rieke, R., et al., "Activated Metals. I. Preparation of Highly Reactive Magnesium Metal", *Journal of the American Chemical Society*, 94:20, pp. 7178–7179, Oct. (1972).

Kündig, E., et al., "262. Low Temperature Grignard Reactions with Pure Mg Slurries. Trapping of Cyclopropylmethyl and Benzocyclobutenylmethyl Grignard Reagents with CO2", *Helvetica Chimica Acta*, vol. 64, Fasc. 8, pp. 2606–2609, (1981). No month.

Bogdanovic, B., et al., "Catalytic Synthesis of Magnesium Hydride under mild Conditions", *Angew. Chem. In. Ed. Engel.,* 19, No. 10, pp. 818–819, (1980). No month.

Bogdanovic, B., et al., "Synthesis and Structure of 1,4–Dimethylanthracenemagnesium–3 thf and –Trichlorodimagnesium–6 thf(1+) Anthracenide", *Angew. Chem. Int. Ed. Engl.,* 24, No. 11, pp. 960–961, (1985). No month.

Lorimer, J., et al., "Chemical Society Reviews Sonochemistry Part1—The Physical Aspects", *The Royal Society of Chemistry,* 16(2), pp. 239–273, (1987). No month.

Lindley, J., et al., "Chemical Society Reviews Sonochemistry Part 2—Synthetic Applications", *The Royal Society of Chemistry,* vol. 16, No. 1, pp. 275–311, Mar. (1987).

Mendel, A., "Reaction of p–(dimethylamino) bromobenzene with "activated" magnesium", *J. Organometal. Chem.,* 6 pp. 97–99, (1966). No month.

CA:109:182368 abs of Huaxue Xuebao by Liao et al 46(6) pp 612–14, 1988.*

CA:77:164789 abs of J Amer Chem Soc by Rieke 94(20) oo 7178–9, 1972.*

* cited by examiner

*Primary Examiner*—Roy V. King
*Assistant Examiner*—Tima McGuthry-Banks
(74) *Attorney, Agent, or Firm*—Scully, Scott, Murphy & Presser

(57) ABSTRACT

The invention relates to activated magnesium metal, to a method of activating magnesium metal and to its use for the preparation of organomagnesium compounds. The activated magnesium metal is obtainable by reacting molten magnesium metal with magnesium hydride; or by heating a mixture of magnesium metal and magnesium hydride until molten.

15 Claims, No Drawings

ACTIVATED MAGNESIUM METAL

FIELD OF THE INVENTION

The present invention relates to activated magnesium metal, to a method of activating magnesium metal, and to the use of said activated magnesium metal for the preparation of organomagnesium compounds.

BACKGROUND OF THE INVENTION

In many areas of synthesis, organometallic compounds, especially organomagnesium compounds, have become indispensable reagents. However, the preparation of these useful reagents continues to present problems. These problems are based, to a certain degree, on the insufficient reactivity of the metals used. Attempts to overcome these difficulties are many and varied since the inertness of the metals used not only has an adverse effect on the efficiency and flexibility of the preparation and process, but also gives rise to potential hazards as a result of uncontrollable spontaneous reactions caused by accumulation of reactants. For example, in the preparation of Grignard compounds, use is made of the mechanical activation of Mg turnings (J. Org. Chem. 1991, 56, 698–703), of potassium-reduced Rieke magnesium (J. Am. Chem. Soc. 1972, 94, 7178, Organic Syntheses, Wiley N.Y., 1988; Collect. Vol.VI, 845), of atomic vaporization of high-purity magnesium into a solvent (Helv. Chim. Acta 1981, 64, 2606), of magnesium anthracene (Angew. Chem., Int. Ed., Engl. 1980, 19, 818 and ibid. 1985, 24, 960) and of ultrasound treatment of commercially available Grignard magnesium (J. Chem. Soc. Rev. 1987, 16, 239 and ibid. 1987, 16, 275).

From the viewpoints of safety, efficiency and ability of scale up, none of the above mentioned laboratory processes has a real chance of moving across into industrial synthesis. It would be extremely beneficial if a process of producing organometallic compounds, especially organomagnesium compounds, was developed that could be used in industrial synthesis.

SUMMARY OF THE INVENTION

Surprisingly, it has now been found that a high-active and also easier-to-handle magnesium metal can be obtained by contacting molten magnesium metal with a small amount of magnesium hydride, or by heating a mixture consisting of magnesium metal and magnesium hydride until molten. Cooling of the molten material gives high-gloss magnesium which is substantially free of oxide skins and other passivating layers. Thus, the activated magnesium metal of the present invention is highly suitable as an active starting material for producing Grignard reagents and Mg-alkylenes. The magnesium obtained in this way in piece form is permeated by many pores, which pores increase the surface area. The high gloss has proven to be stable under customary environmental conditions.

Surprisingly, the observed passivation toward customary environmental influences is accompanied by activation of the metal treated according to the present invention for organometallic reactions.

DETAILED DESCRIPTION OF THE INVENTION

A first embodiment of the present invention thus consists of activated magnesium metal obtainable by reacting molten magnesium with magnesium hydride.

A further embodiment of the present invention consists of a method of preparing activated magnesium metal by reacting molten magnesium metal with magnesium hydride.

A still further embodiment of the present invention is directed to activated magnesium metal which is obtained by heating a mixture of magnesium metal and magnesium hydride until molten.

For the purposes of the present invention, the term "magnesium" includes not only pure magnesium, but also magnesium-based alloys which comprise at least 90% by weight of magnesium.

The quantitative ratio of magnesium metal to magnesium hydride is of lesser importance in the present invention. However, for the purposes of the present invention, particular preference is given to a quantitative ratio of magnesium metal to magnesium hydride in the range from 1:0.0005 to 1:0.1, more preferably from 1:0.005 to 1:0.05, and most preferably from 1:0.005 to 1:0.025. Within the given ranges, cost considerations play a particular role, as does the possibility of repeating the treatment or reaction several times.

A completely surprising finding for the person skilled in the art is also that even coarse particles of magnesium metal activated using magnesium hydride are, for example, suitable for the reaction with halogenated organo compounds. Turnings, in the order of magnitude from 4 to 5 mm react, without significant induction period, virtually quantitatively to give the desired organomagnesium halide compound.

A further preferred embodiment of the present invention thus consists of the use of the inventive activated magnesium metal for the preparation of organomagnesium compounds, wherein the activated magnesium metal, is preferably in the form of powders, turnings or in piece form. In accordance with this aspect of the present invention, the activated magnesium metal is reacted in a manner known per se with organic compounds known per se. At this point, the preparation of Grignard compounds is specifically mentioned. When a Grignard compound is to be prepared, it is prepared utilizing preparation processes well known to those skilled in the art. Since such processes are well known, a detailed description of the same is not provided herein.

The commercial magnesium employed for the process has a purity of $\geq 99.5\%$. A suitable magnesium hydride is $MgH_2$ obtained from the elements Mg and H at high temperatures by a conventional autocatalysis route described, for example, in EP 0 490 156 A, or any other magnesium hydride produced by another method.

The activated magnesium metal obtained by the method according to the present invention exhibits visible differences compared with untreated commercial magnesium metal. The fracture and cut surfaces of the highly porous and fissured metal are shiny bright silver and, even after storage for weeks in a customary atmosphere, do not exhibit any tendency toward tarnishing.

The activated magnesium metal prepared by a melt-metallurgical process also has a brittleness which is significantly increased compared with untreated magnesium metal, making comminution of the coarsely particulate material very easy.

Grignard compounds are optionally prepared in-situ by reacting magnesium turnings with alkyl or aryl halides, usually in anhydrous solvents.

The final evidence for the increase in activity comes from the direct reactivity comparison of the magnesium metal prepared by the method according to the present invention with commercially available Grignard magnesium turnings which have been activated in accordance with the prior art.

In the tradition of some works (ibid.) concerned with this problem, J. Organometal. Chem. 6, 97–99 (1966) describes the reaction between p-(dimethylamino)bromobenzene and activated magnesium. Magnesium turnings are stirred under inert gas for 24 hours or longer and only in this manner attain an activity which enables the reaction with p-(dimethylamino)bromobenzene to be carried out in boiling tetrahydrofuran without the use of initiators which are customary here, such as, for example, iodine or alkyl halides (see also Houben-Weyl, Methoden der Organischen Chemie, 13/ 2a, p. 58). The reaction time is then 3 hours.

The magnesium metal prepared by the method according to the present invention requires neither mechanical nor chemical activation in order to react virtually quantitatively with p-(dimethylamino)bromobenzene in THF to give the corresponding Grignard compound within one hour.

The activity of the magnesium metal prepared by the method according to the present invention could not have been foreseen by the person skilled in the art; therefore the activated metal of the present invention is a useful starting material in the synthesis of organomagnesium compounds.

The following examples are given to illustrate the present invention and to demonstrate some advantages that can arise therefrom.

EXAMPLE 1

Preparation of active magnesium

A steel capsule was charged with a mixture consisting of 500 g of a 99.5% by weight magnesium powder and 10 g of a 95% by weight autocatalytically prepared magnesium hydride (Tego Magnan®) and heated to 750° C. in an inerted induction furnace. The temperature was maintained for about 3minutes; the reaction mixture was then cooled. Cooling gave a regulus permeated by shiny bright silver voids which, even after storage for 3 months in the customary atmosphere, did not exhibit a tendency to tarnish at the void surfaces generated by the process, or at the bright silver saw cut surfaces. A low-speed drill was used to obtain Mg turnings measuring from about 2 to 5 mm.

EXAMPLE 2

Use of the active magnesium for the preparation of p(dimethylamino)phenylmagnesium bromide 0.9 g (0.037 mol) of the Mg turnings of Example 1 were placed in a 250 ml four-necked flask with attached condenser and dropping funnel and with magnetic stirring, and covered with 80 ml of absolute tetrahydrofuran and then heated to 55° C. A solution consisting of 7.4 g (0.037 mol) of p(dimethylamino)bromobenzene in 55 ml of absolute tetrahydrofuran was slowly added dropwise thereto. After about 12 ml of the halide solution had been added, the Grignard reaction started (gray coloration and slight gassing). By adding the remaining solution dropwise in an uninterrupted manner, the reaction mixture was maintained at a temperature of 64° C. When the addition was complete, the mixture was heated to slight reflux. After a total reaction time of 1 hour, the deep black mixture was left to cool. Acidimetric titration of a clear slightly yellowish aliquot obtained after centrifugation proved a virtually quantitative Mg conversion ($\geqq 98\%$).

While the present invention has been particularly shown and described with respect to preferred embodiments thereof, it will be understood by those skilled in the art that the foregoing and other changes in form and detail may be made without departing from the scope and spirit of the present invention. It is therefore intended that the present invention should not be limited to the exact forms described and illustrated but fall within the appended claims.

What is claimed is:

1. A method of activating magnesium metal comprising reacting molten magnesium metal with magnesium hydride.

2. The method of claim 1, wherein said molten magnesium metal and said magnesium hydride are reacted at a quantitative ratio of magnesium metal to magnesium hydride of from 1:0.0005 to 1:0.1.

3. The method of claim 2, wherein said quantitative ratio of magnesium metal to magnesium hydride is from 1:0.005 to 1:0.05.

4. The method of claim 3, wherein said quantitative ratio of magnesium metal to magnesium hydride is from 1:0.005 to 1:0.025.

5. The method of claim 1, wherein said molten magnesium metal is pure magnesium metal or a magnesium-based alloy comprising at least 90% by weight magnesium.

6. Activated magnesium metal obtained by the method of claim 1, said activated magnesium metal is substantially free of oxide skins and other passivating layers.

7. A method of activating magnesium metal comprising heating a mixture comprising magnesium metal and magnesium hydride until molten.

8. The method of claim 7, wherein said magnesium metal and said magnesium hydride are used at a quantitative ratio of from 1:0.0005 to 1:0.1.

9. The method of claim 8, wherein said quantitative ratio of magnesium metal to magnesium hydride is from 1:0.005 to 1:0.05.

10. The method of claim 9, wherein said quantitative ratio of magnesium metal to magnesium hydride is from 1:0.005 to 1:0.025.

11. The method of claim 7, wherein said magnesium metal is pure magnesium or a magnesium-based alloy comprising at least 90% by weight magnesium.

12. Activated magnesium metal obtained by the method of claim 7, wherein said activated magnesium metal is substantially free of oxide skins and other passivating layers.

13. A method of preparing an organomagnesium compound with activated magnesium metal, wherein said activated magnesium metal is formed by either (i) reacting molten magnesium with magnesium hydride or (ii) heating a mixture comprising magnesium metal and magnesium hydride until molten.

14. The method of claim 13, wherein said organomagnesium compound is a Grignard compound.

15. The method of claim 13, wherein said activated magnesium metal is in the form of powder, turnings or in piece form.

* * * * *